US010123837B2

United States Patent
Brannan

(10) Patent No.: US 10,123,837 B2
(45) Date of Patent: *Nov. 13, 2018

(54) ENERGY-DELIVERY DEVICES WITH FLEXIBLE FLUID-COOLED SHAFT, INFLOW / OUTFLOW JUNCTIONS SUITABLE FOR USE WITH SAME, AND SYSTEMS INCLUDING SAME

(71) Applicant: COVIDIEN LP, Mansfield, MA (US)

(72) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 613 days.

This patent is subject to a terminal disclaimer.

(21) Appl. No.: 14/690,963

(22) Filed: Apr. 20, 2015

(65) Prior Publication Data
US 2015/0223884 A1 Aug. 13, 2015

Related U.S. Application Data

(63) Continuation of application No. 12/985,179, filed on Jan. 5, 2011, now Pat. No. 9,017,319.

(51) Int. Cl.
*A61B 18/18* (2006.01)
*A61B 18/14* (2006.01)
*A61B 18/00* (2006.01)

(52) U.S. Cl.
CPC ...... *A61B 18/1815* (2013.01); *A61B 18/1492* (2013.01); *A61B 2018/00023* (2013.01);
(Continued)

(58) Field of Classification Search
CPC ........ A61B 18/1815; A61B 2018/1823; A61B 2018/183; A61B 2018/1838; A61B 2018/1846; A61B 2018/1853; A61B 2018/1861; A61B 2018/1869; A61B 2018/1876; A61B 2018/1884; A61B 2018/1892
See application file for complete search history.

(56) References Cited

U.S. PATENT DOCUMENTS

D263,020 S 2/1982 Rau, III
4,632,127 A 12/1986 Sterzer
(Continued)

FOREIGN PATENT DOCUMENTS

CN 1103807 A 6/1995
DE 390937 C 3/1924
(Continued)

OTHER PUBLICATIONS

Search Report EP 09010873.9 extended dated Nov. 13, 2009.
(Continued)

*Primary Examiner* — Jaymi Della

(57) ABSTRACT

An energy-delivery device suitable for delivery of energy to tissue includes an antenna assembly, a chamber defined about the antenna assembly, and a cable having a proximal end suitable for connection to an electrosurgical energy source. The energy-delivery device also includes a flexible, fluid-cooled shaft coupled in fluid communication with the chamber. The flexible, fluid-cooled shaft is configured to contain a length of the cable therein and adapted to remove heat along the length of the cable during delivery of energy to the antenna assembly.

19 Claims, 5 Drawing Sheets

(52) U.S. Cl.
CPC ............... *A61B 2018/1861* (2013.01); *A61B 2018/1892* (2013.01)

(56) References Cited

U.S. PATENT DOCUMENTS

| | | | |
|---|---|---|---|
| 4,632,128 | A | 12/1986 | Paglione et al. |
| D295,893 | S | 5/1988 | Sharkany et al. |
| D295,894 | S | 5/1988 | Sharkany et al. |
| 4,813,429 | A | 3/1989 | Eshel et al. |
| 5,129,396 | A | 7/1992 | Rosen et al. |
| 5,275,597 | A * | 1/1994 | Higgins ............... A61B 17/22 606/33 |
| 5,281,217 | A | 1/1994 | Edwards et al. |
| 5,344,435 | A | 9/1994 | Turner et al. |
| 5,358,515 | A | 10/1994 | Hurter et al. |
| 5,369,251 | A | 11/1994 | King et al. |
| 5,405,346 | A | 4/1995 | Grundy et al. |
| 5,861,021 | A | 1/1999 | Thome et al. |
| 5,904,709 | A | 5/1999 | Arndt et al. |
| 6,007,571 | A | 12/1999 | Neilson et al. |
| D424,694 | S | 5/2000 | Tetzlaff et al. |
| D425,201 | S | 5/2000 | Tetzlaff et al. |
| 6,223,085 | B1 | 4/2001 | Dann et al. |
| 6,241,666 | B1 | 6/2001 | Pomeranz et al. |
| 6,289,249 | B1 | 9/2001 | Arndt et al. |
| D449,886 | S | 10/2001 | Tetzlaff et al. |
| D457,958 | S | 5/2002 | Dycus et al. |
| D457,959 | S | 5/2002 | Tetzlaff et al. |
| 6,440,158 | B1 | 8/2002 | Saab |
| 6,496,737 | B2 | 12/2002 | Rudie et al. |
| 6,522,932 | B1 | 2/2003 | Kuzma et al. |
| 6,575,969 | B1 | 6/2003 | Rittman, III et al. |
| 6,640,139 | B1 | 10/2003 | Ueberle |
| 6,699,241 | B2 | 3/2004 | Rappaport et al. |
| D496,997 | S | 10/2004 | Dycus et al. |
| D499,181 | S | 11/2004 | Dycus et al. |
| 6,905,510 | B2 | 6/2005 | Saab |
| 6,953,461 | B2 | 10/2005 | McClurken et al. |
| D525,361 | S | 7/2006 | Hushka |
| 7,113,832 | B2 | 9/2006 | Longo |
| D531,311 | S | 10/2006 | Guerra et al. |
| D533,942 | S | 12/2006 | Kerr et al. |
| D535,027 | S | 1/2007 | James et al. |
| D541,418 | S | 4/2007 | Schechter et al. |
| D541,938 | S | 5/2007 | Kerr et al. |
| 7,311,703 | B2 | 12/2007 | Turovskiy et al. |
| 7,335,198 | B2 | 2/2008 | Eggers et al. |
| D564,662 | S | 3/2008 | Moses et al. |
| D606,203 | S | 12/2009 | Husheer et al. |
| D613,412 | S | 4/2010 | DeCarlo |
| 7,777,130 | B2 | 8/2010 | Deborski et al. |
| 9,017,319 | B2 | 4/2015 | Brannan |
| 2004/0002747 | A1 | 1/2004 | Ryan et al. |
| 2005/0015081 | A1 * | 1/2005 | Turovskiy ............... A61B 18/18 606/33 |
| 2005/0059966 | A1 | 3/2005 | McClurken et al. |
| 2005/0113893 | A1 | 5/2005 | Saab |
| 2005/0149010 | A1 | 7/2005 | Turovskiy et al. |
| 2005/0245920 | A1 | 11/2005 | Vitullo et al. |
| 2007/0027449 | A1 | 2/2007 | Godara et al. |
| 2007/0142829 | A1 | 6/2007 | Ahn et al. |
| 2007/0185554 | A1 | 8/2007 | Appling et al. |
| 2007/0219544 | A1 * | 9/2007 | Gowda ............... A61N 5/0601 606/16 |
| 2007/0287994 | A1 | 12/2007 | Patel |
| 2008/0009927 | A1 | 1/2008 | Vilims |
| 2008/0125775 | A1 | 5/2008 | Morris |
| 2008/0161890 | A1 * | 7/2008 | Lafontaine ......... A61B 18/1492 607/105 |
| 2008/0308256 | A1 | 12/2008 | Deborski et al. |
| 2009/0012513 | A1 | 1/2009 | Utley et al. |
| 2009/0138005 | A1 | 5/2009 | Prakash et al. |
| 2009/0187180 | A1 * | 7/2009 | Brannan ............... A61B 18/18 606/33 |
| 2009/0222002 | A1 * | 9/2009 | Bonn ............... A61B 18/18 606/33 |
| 2009/0248006 | A1 * | 10/2009 | Paulus ............... A61B 18/18 606/33 |
| 2009/0295674 | A1 * | 12/2009 | Bonn ............... A61B 18/18 343/872 |
| 2010/0053015 | A1 | 3/2010 | Willyard |
| 2010/0087808 | A1 | 4/2010 | Paulus |
| 2010/0097284 | A1 | 4/2010 | Brannan et al. |
| 2010/0121319 | A1 | 5/2010 | Chu et al. |
| 2010/0234839 | A1 | 9/2010 | Smith et al. |
| 2010/0243287 | A1 | 9/2010 | Deborski et al. |
| 2010/0286681 | A1 | 11/2010 | Podhajsky |
| 2010/0298822 | A1 | 11/2010 | Behnke |
| 2010/0305559 | A1 | 12/2010 | Brannan et al. |
| 2011/0208177 | A1 | 8/2011 | Brannan |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 836 868 A2 | 4/1998 |
| EP | 0 882 955 A1 | 12/1998 |
| EP | 1 159 926 A2 | 12/2001 |
| EP | 1506757 A1 | 2/2005 |
| EP | 1 905 375 A1 | 4/2008 |
| EP | 2098184 A1 | 9/2009 |
| EP | 2128929 A1 | 12/2009 |
| EP | 2158868 A1 | 3/2010 |
| EP | 2255742 A1 | 12/2010 |
| EP | 2322113 A1 | 5/2011 |
| EP | 2399646 A1 | 12/2011 |
| FR | 179 607 | 11/1906 |
| FR | 1 275 415 A | 11/1961 |
| FR | 1 347 865 A | 1/1964 |

(56) References Cited

FOREIGN PATENT DOCUMENTS

| | | |
|---|---|---|
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 7-275247 A | 10/1995 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2001231870 A | 8/2001 |
| JP | 2003-518979 A | 6/2003 |
| JP | 2004329764 A | 11/2004 |
| JP | 2005-507736 A | 3/2005 |
| JP | 2005118357 A | 5/2005 |
| JP | 2006507865 A | 3/2006 |
| JP | 2007222689 A | 9/2007 |
| JP | 2007532024 A | 11/2007 |
| JP | 2007-535370 A | 12/2007 |
| JP | 2008142467 A | 6/2008 |
| JP | 2009521967 A | 6/2009 |
| JP | 2009207898 A | 9/2009 |
| JP | 2009-285463 A | 12/2009 |
| JP | 2009-285493 A | 12/2009 |
| JP | 2010110579 A | 5/2010 |
| JP | 2010269148 A | 12/2010 |
| JP | 2010279696 A | 12/2010 |
| SU | 166452 | 1/1965 |
| SU | 401367 A1 | 10/1973 |
| SU | 727201 A2 | 4/1980 |
| WO | 00/36985 A2 | 6/2000 |
| WO | 2004047659 A2 | 6/2004 |
| WO | 2005/011049 A2 | 2/2005 |
| WO | 2007/006158 A1 | 1/2007 |
| WO | 2008028980 A2 | 3/2008 |
| WO | 2009094422 A1 | 7/2009 |
| WO | 2009/124301 A1 | 10/2009 |
| WO | 2010/035831 A1 | 4/2010 |
| WO | 2011063061 A2 | 5/2011 |

OTHER PUBLICATIONS

Search Report EP 09010877.0 extended dated Dec. 3, 2009.
Search Report EP 09151621 dated Jun. 18, 2009.
Search Report EP 09156861.8 dated Aug. 4, 2009.
Search Report EP 09161502.1 dated Sep. 2, 2009.
Search Report EP 09161502.1 extended dated Oct. 30, 2009.
Search Report EP 09165976.3 extended dated Mar. 17, 2010.
Search Report EP 09166708 dated Oct. 15, 2009.
Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
European Search Report, Application No. EP 14 16 2347 dated Sep. 30, 2014.
European Search Report for European Application No. 11010093.0 dated Mar. 20, 2012.
European Search Report for European Application No. 11010176.3 dated Mar. 19, 2012.
European Search Report for European Application No. 11010177.1 dated May 2, 2012.
European Search Report for European Application No. 11010175.5 dated Apr. 26, 2012.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/582,857, filed Oct. 21, 2009, Charles D. Allen.
U.S. Appl. No. 12/606,769, filed Oct. 27, 2009, Joseph D. Brannan.
U.S. Appl. No. 12/607,221, filed Oct. 28, 2009, Joseph D. Brannan.
U.S. Appl. No. 12/607,268, filed Oct. 28, 2009, Joseph D. Brannan.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.

(56) References Cited

OTHER PUBLICATIONS

U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/877,182, filed Sep. 8, 2010, Robert B. Cunningham.
U.S. Appl. No. 12/910,442, filed Oct. 22, 2010, Robert B. Cunningham.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
Japanese Office Action and English Translation from Japanese Appl. No. 2011-287386 dated Mar. 29, 2016.
European Examination Report from Appl. No. 11010176.3 dated Nov. 7, 2012.
Extended European Search Report from Appl. No. 13004834.1 dated Jan. 8, 2014.
Extended European Search Report from Appl. No. 14200555.2 dated Apr. 22, 2015.
European Examination Report from Appl. No. 11010175.5 dated Jul. 25, 2013.
Extended European Search Report from Appl. No. 14152429.8 dated Apr. 9, 2014.
Extended European Search Report from Appl. No. 13004659.2 dated Feb. 17, 2014.
Japanese Office Action from Appl. No. 2011-287386 dated Aug. 4, 2015.
Japanese Office Action from Appl. No. 2011-283289 dated Oct. 6, 2015.
Japanese Office Action from Japanese Appl. No. 2011-287386 dated Dec. 8, 2015.
Decision of Rejection from Japanese Appl. No. 2011-283440 dated May 24, 2016.
Japanese Office Action from Appl. No. JP 2011-282887 dated Aug. 4, 2015.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radial, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.

(56) References Cited

OTHER PUBLICATIONS

Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" AMZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.-Medical Professionals: Targis.TM. Technology (Date Unknown). "Overcoming the Challenge" located at: <http://www.urologix.com!medicaUtechnology.html> last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
Extended European Search Report, Application No. EP 16161331.0, dated Oct. 26, 2016.
Extended European Search Report, Application No. EP 16182779.5, dated Nov. 14, 2016.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.

(56) References Cited

OTHER PUBLICATIONS

Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite Element Codes to Model Electrical Heating and Non.cndot.LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Japanese Office Action with English language translation from Appl. No. 2016-095550 dated Feb. 28, 2017.
Reconsideration Report from Japanese Appl. No. 2011-287386 dated Sep. 7, 2016.
Pre-trial Examination Report from Japanese Appl. No. 2011-283289 dated Sep. 13, 2016.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
Japanese Office Action issued in Appl. No. JP 2017-131183 dated Jul. 3, 2018, together with English translation (4 pages).

* cited by examiner

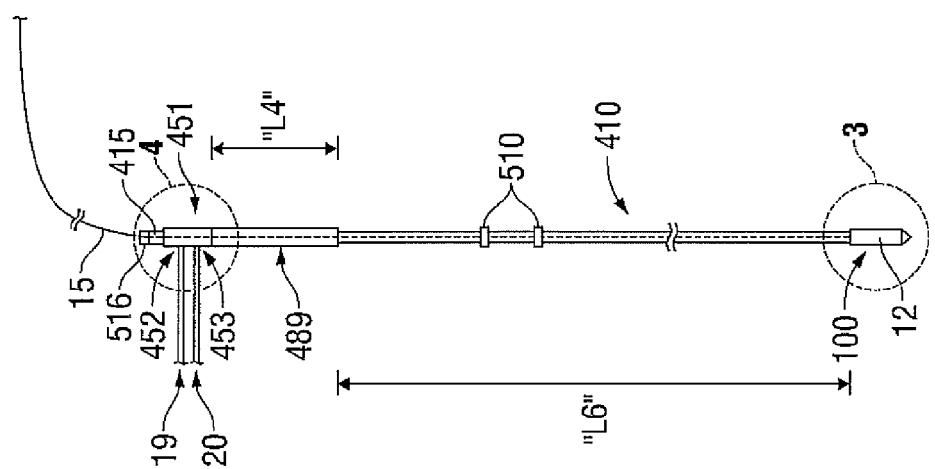
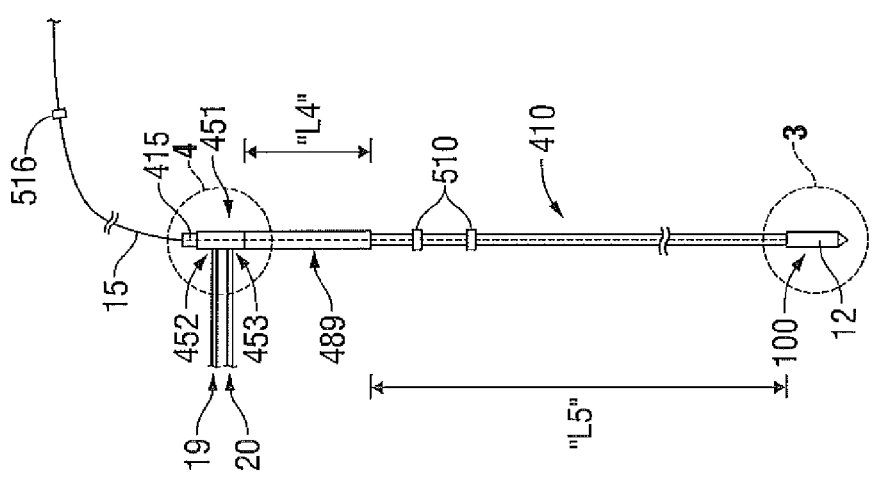

ENERGY-DELIVERY DEVICES WITH FLEXIBLE FLUID-COOLED SHAFT, INFLOW / OUTFLOW JUNCTIONS SUITABLE FOR USE WITH SAME, AND SYSTEMS INCLUDING SAME

CROSS-REFERENCE TO RELATED APPLICATIONS

This application is a continuation application claiming the benefit of and priority to U.S. application Ser. No. 12/985,179, filed on Jan. 5, 2011, now U.S. Pat. No. 9,017,319, the entire contents of which is incorporated herein by reference.

BACKGROUND

1. Technical Field

The present disclosure relates to electrosurgical devices suitable for use in tissue ablation applications and, more particularly, to energy-delivery devices with a flexible, fluid-cooled shaft, inflow/outflow junctions suitable for use with the same, and systems including the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

The particular type of tissue ablation procedure may dictate a particular ablation volume in order to achieve a desired surgical outcome. Ablation volume is correlated with antenna design, antenna performance, antenna impedance, ablation time and wattage, and tissue characteristics, e.g., tissue impedance.

Fluid-cooled or dielectrically-buffered microwave devices may be used in ablation procedures. Cooling the ablation probe may enhance the overall heating pattern of the antenna, prevent damage to the antenna and prevent harm to the clinician or patient. Because of the small temperature difference between the temperature required for denaturing malignant cells and the temperature normally injurious to healthy cells, a known heating pattern and precise temperature control is needed to lead to more predictable temperature distribution to eradicate the tumor cells while minimizing the damage to surrounding normal tissue.

During certain procedures, it can be difficult for the surgeon to deploy an ablation probe, e.g., between closely spaced boundaries of tissue structures, to reach the location of the ablation site. Currently available microwave ablation devices may not be suitable for use during open surgical procedures when the surgeon is trying to ablate a lesion that is not easily accessed via a midline incision. A cable assembly connecting the ablation probe to a generator may come into contact with a patient and may facilitate potentially unwanted heat transfer.

SUMMARY

The present disclosure relates to an energy-delivery device suitable for delivery of energy to tissue including an antenna assembly, a chamber defined about the antenna assembly, and a cable assembly having a proximal end suitable for connection to an electrosurgical energy source. The energy-delivery device also includes a flexible, fluid-cooled shaft coupled in fluid communication with the chamber. The flexible, fluid-cooled shaft is configured to contain a length of the cable assembly therein and adapted to remove heat along the length of the cable assembly during delivery of energy to the antenna assembly.

The present disclosure also relates to an ablation device including a feedline and an antenna assembly. The feedline includes an inner conductor having a distal end, an outer conductor coaxially disposed around the inner conductor and having a distal end, and a dielectric material disposed therebetween. The antenna assembly includes an electrically-conductive proximal arm having a proximal end and a distal end, and an electrically-conductive distal arm including a proximal portion having an outer diameter and a distal portion having an outer diameter less than the outer diameter of the proximal portion. The proximal end of the proximal arm is electrically coupled to and coaxially disposed about the distal end of the outer conductor. The antenna assembly also includes a junction member. The proximal arm and the distal arm align at the junction member and are spaced apart a length by the junction member, thereby defining a feed gap therebetween.

The present disclosure also relates to a system including an electrosurgical energy source and an ablation device operably associated with the electrosurgical energy source. The ablation device includes a feedline and an antenna assembly operatively coupled to the feedline. The feedline includes an inner conductor having a distal end, an outer conductor coaxially disposed around the inner conductor and having a distal end, and a dielectric material disposed therebetween. The antenna assembly includes an electrically-conductive proximal arm having a proximal end and a distal end, and an electrically-conductive distal arm including a proximal portion having an outer diameter and a distal portion having an outer diameter less than the outer diameter of the proximal portion. The proximal end of the proximal arm is electrically coupled to and coaxially disposed about the distal end of the outer conductor. The proximal arm defines a first cavity therein extending from the distal end of the outer conductor to the distal end of the proximal arm. The proximal portion of the distal arm defines a second cavity therein. The antenna assembly also includes a junction member at least partially disposed in the first and second cavities. The proximal arm and the distal arm align at the junction member and are spaced apart a length by the junction member, thereby defining a feed gap therebetween.

The present disclosure also relates to an inflow/outflow junction suitable for connection to a first tubular member disposed around a transmission line and defining a fluid inflow conduit therebetween and a second tubular member disposed around the first tubular member and defining a fluid outflow conduit therebetween. The inflow/outflow junction includes a housing adapted to be coupled in fluid communication with a coolant supply system. The housing includes an outer wall and an inner wall cooperatively defining a fluid inlet chamber and a fluid outlet chamber. The inner wall is configured to define an opening in the fluid inlet chamber to allow the fluid inlet chamber to be connectable in fluid communication with the fluid inflow conduit. The outer wall is configured to define an opening in the fluid outlet chamber to allow the fluid outlet chamber to be connectable in fluid communication with the fluid outflow conduit.

The present disclosure also relates to a system including an electrosurgical energy source and an energy-delivery device operably associated with the electrosurgical energy source. The energy-delivery device includes an end-cap assembly defining a chamber therein, an antenna assembly disposed in the chamber; and a cable assembly configured to deliver energy from the electrosurgical energy source to the antenna assembly. The system also includes a flexible, extendable/retractable fluid-cooled shaft coupled in fluid communication with the chamber, wherein the flexible, extendable/retractable fluid-cooled shaft is configured to contain a length of the cable assembly therein and adapted to remove heat along the length of the cable assembly during delivery of energy to the antenna assembly.

BRIEF DESCRIPTION OF THE DRAWINGS

Objects and features of the presently disclosed energy-delivery devices with a flexible, fluid-cooled shaft and systems including the same will become apparent to those of ordinary skill in the art when descriptions of various embodiments thereof are read with reference to the accompanying drawings, of which:

FIG. 5 is a schematic diagram of the flexible, extendable/retractable fluid-cooled shaft and the inflow/outflow junction of FIG. 4 shown in a retracted configuration in accordance with an embodiment of the present disclosure; and FIG. 6 is a schematic diagram of the flexible, extendable/retractable fluid-cooled shaft and the inflow/outflow junction of FIG. 4 shown in an extended configuration in accordance with an embodiment of the present disclosure.

DETAILED DESCRIPTION

Figure 1:
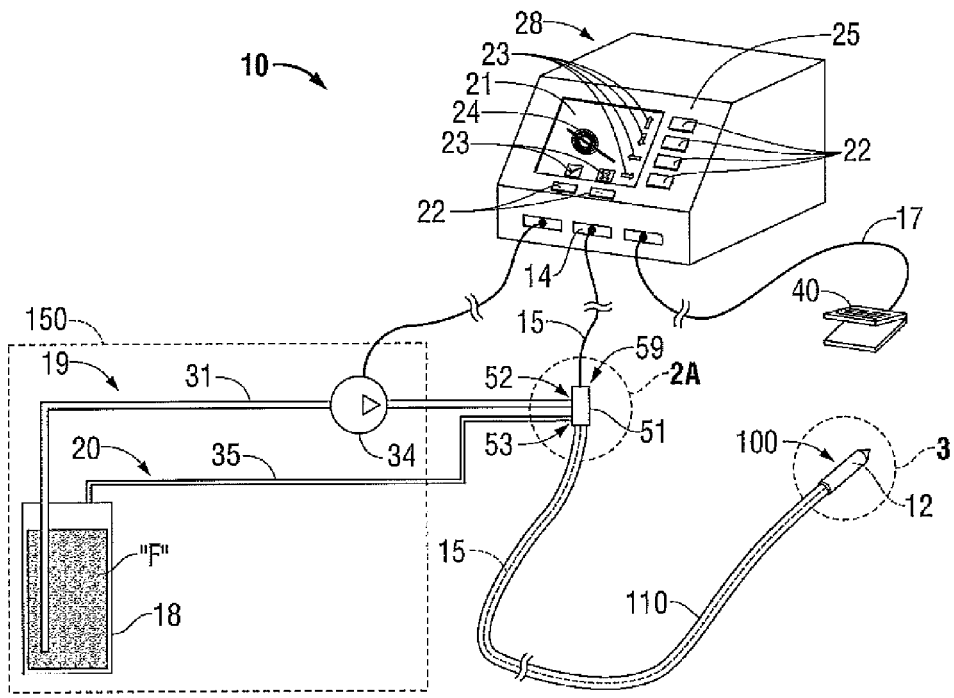
FIG. 1 is a schematic diagram of an electrosurgical system including an energy-delivery device with a flexible, fluid-cooled shaft in accordance with an embodiment of the present disclosure.

Hereinafter, embodiments of energy-delivery devices with a flexible, fluid-cooled shaft and systems including the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as, for example, microwave ablation, radiofrequency (RF) ablation, or microwave or RF ablation-assisted resection.

As it is used in this description, "energy applicator" generally refers to any device that can be used to transfer energy from a power generating source, such as a microwave or RF electrosurgical generator, to tissue. For the purposes herein, the term "energy applicator" is interchangeable with the term "energy-delivery device". As it is used in this description, "transmission line" generally refers to any transmission medium that can be used for the propagation of signals from one point to another. As it is used in this description, "fluid" generally refers to a liquid, a gas or both.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

Various embodiments of the present disclosure provide an energy-delivery device with a flexible, fluid-cooled shaft. Embodiments may be suitable for utilization in open surgical applications. Embodiments may be suitable for utilization with hand-assisted, endoscopic and laparoscopic surgical procedures. Embodiments may be implemented using electromagnetic radiation at microwave frequencies, RF frequencies or at other frequencies. An electrosurgical system including the presently disclosed energy-delivery device with a flexible, fluid-cooled shaft disposed in fluid communication with a coolant supply system via an inflow/outflow junction 51 according to various embodiments is designed and configured to operate at frequencies between about 300 MHz and about 10 GHz.

Various embodiments of the presently disclosed energy-delivery device with a flexible, fluid-cooled shaft are suitable for microwave or RF ablation and for use to pre-coagulate tissue for microwave or RF ablation-assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna or RF electrode.

FIG. 1 shows an electrosurgical system 10 according to an embodiment of the present disclosure that includes an energy applicator or probe 100 with a flexible, fluid-cooled shaft 110 coupled in fluid communication with a coolant supply system 150 via an inflow/outflow junction 51. An embodiment of an energy applicator, such as the probe 100 of FIG. 1, in accordance with the present disclosure, is shown in more detail in FIG. 3. It is to be understood, however, that other probe embodiments may also be used.

Probe 100, which is described in more detail later in this disclosure, generally includes an antenna assembly 12 having a distal radiating portion (e.g., "R" shown in FIG. 3). As shown in FIG. 1, the probe 100 is operably coupled by a flexible, transmission line 15 (also referred to herein as a cable assembly) to a connector 14, which further operably connects the probe 100 to an electrosurgical power generating source 28, e.g., a microwave or RF electrosurgical generator. Cable assembly 15 may include a proximal end suitable for connection to the electrosurgical power generating source 28. At least a portion of the cable assembly 15 (e.g., a length that may potentially transfer heat to a patient's body during a procedure) is disposed within the flexible, fluid-cooled shaft 110.

Figure 3:
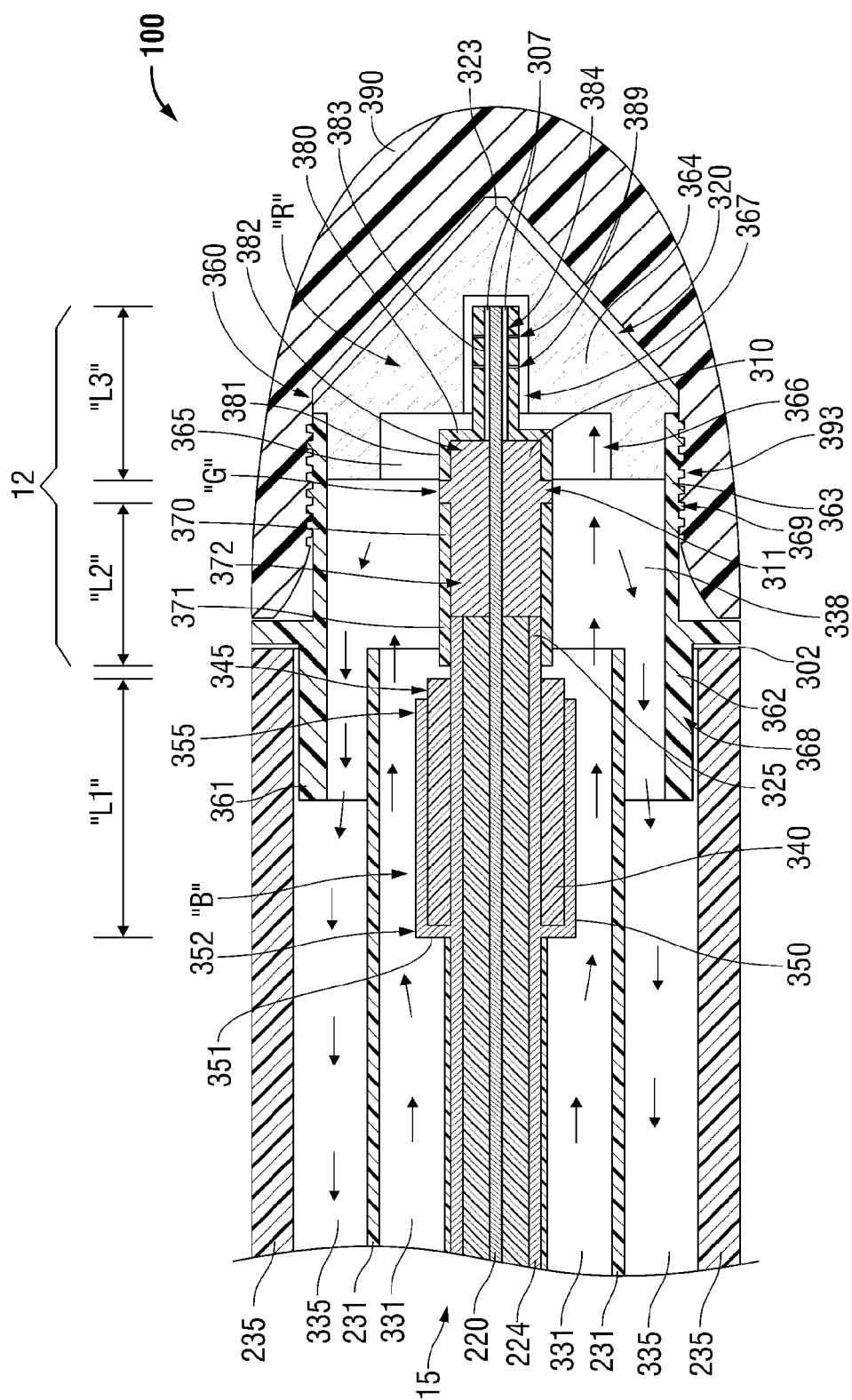
FIG. 3 is an enlarged, cross-sectional view of the indicated area of detail of FIG. 1 showing a portion of a flexible, fluid-cooled shaft and an energy-delivery device adapted to be coupled in fluid communication therewith in accordance with an embodiment of the present disclosure.

In some embodiments, the probe 100 includes a balun structure (e.g., "B" shown in FIG. 3). Balun structure "B", which is described in more detail later in this disclosure, generally includes a balun insulator (e.g., 340 shown in FIG. 3) and a conductive balun sleeve (e.g., 350 shown in FIG. 3) disposed around the outer peripheral surface of the balun insulator, or portions thereof, and may include a balun short (e.g., 351 shown in FIG. 3).

According to various embodiments, the flexible, fluid-cooled shaft 110 is configured to circulate coolant fluid "F", e.g., saline, water or other suitable coolant fluid, to remove heat that may generated along the length of the cable assembly 15, or portions thereof, during the delivery of energy, e.g., RF or microwave energy, to the probe 100. As cooperatively shown in FIGS. 1 and 2A, the shaft 110 includes a cable assembly 15, an inner tubular member 231 disposed around the cable assembly 15 and defining a lumen or fluid inflow conduit 331 therebetween, and an outer tubular member 235 disposed around the inner tubular member 231 and defining a lumen or fluid outflow conduit 335 therebetween. Outer tubular member 235 and the inner tubular member 231 are adapted to circulate coolant fluid "F" therethrough, and may include baffles, multiple lumens, flow restricting devices, or other structures that may redirect, concentrate, or disperse flow depending on their shape. In some embodiments, the inner tubular member 231 is coaxially disposed about the cable assembly 15, and the outer tubular member 235 is coaxially disposed about the inner tubular member 231. The size and shape of the inner tubular member 231, the outer tubular member 235, the fluid inflow conduit 331, and fluid outflow conduit 335 may be varied from the configuration depicted in FIG. 2A.

In some embodiments, at least a portion of the inner tubular member 231 and/or at least a portion of the outer tubular member 235 (e.g., a distal portion) may include an integrated, spiraling metallic wire to add shape-memory properties to the flexible, fluid-cooled shaft 110, e.g., to aid in placement of the probe 100. In some embodiments, the inner tubular member 231 and/or the outer tubular member 235 may increase in stiffness and exhibit increased shape-memory properties along their length distally toward the antenna assembly 12.

Shaft 110 may have a variable length from a proximal end of the antenna assembly 12 to a distal end of inflow/outflow junction 51, e.g., ranging from a length of about three feet to about six feet. Shaft 110 may have any suitable outer diameter "D". In some embodiments, the shaft 110 may have an outer diameter "D" in a range from about 0.030 inches to about 0.110 inches. Various components of the shaft 110 may be formed of suitable, electrically-conductive materials, e.g., copper, gold, silver, or other conductive metals or metal alloys having similar conductivity values. Electrically-conductive materials used to form the cable assembly 15 may be plated with other materials, e.g., other conductive materials, such as gold or silver, to improve their properties, e.g., to improve conductivity, decrease energy loss, etc.

Cable assembly 15 may be any suitable, flexible transmission line. Cable assembly 15 may include an inner conductor 220, a dielectric material 222 coaxially surrounding the inner conductor 220, and an outer conductor 224 coaxially surrounding the dielectric material 222. Antenna assembly 12 may be formed from a portion of the inner conductor 220 that extends distal to the shaft 110 into the antenna assembly 12. Dielectric material 222 may be formed from any suitable, flexible, dielectric material, including, but not limited to, polyethylene, polyethylene terephthalate, polyimide, or polytetrafluoroethylene (PTFE) (e.g., Teflon®, manufactured by E. I. du Pont de Nemours and Company of Wilmington, Del., United States). Inner conductor 220 and the outer conductor 224 may be formed from any suitable electrically-conductive material. In some embodiments, the inner conductor 210 is formed from a first electrically-conductive material (e.g., stainless steel) and the outer conductor 224 is formed from a second electrically-conductive material (e.g., copper). In some embodiments, the outer conductor 224 is formed of one or more layers of braided metallic wires, e.g., to improve flexibility characteristics of the cable assembly 15. Cable assembly 15 may be provided with an outer coating or sleeve 226 disposed about the outer conductor 224. Sleeve 226 may be formed of any suitable insulative material, and may be may be applied by any suitable method, e.g., heat shrinking, over-molding, coating, spraying dipping, powder coating, baking and/or film deposition.

Electrosurgical power generating source 28 may be any generator suitable for use with electrosurgical devices, and may be configured to provide various frequencies of electromagnetic energy. In some embodiments, the electrosurgical power generating source 28 is configured to provide microwave energy at an operational frequency from about 300 MHz to about 2500 MHz. In other embodiments, the electrosurgical power generating source 28 is configured to provide microwave energy at an operational frequency from about 300 MHz to about 10 GHz.

Electrosurgical power generating source 28 may include a user interface 25 in operable communication with a processor unit (not shown). The processor unit may be any type of computing device, computational circuit, or any type of processor or processing circuit capable of executing a series of instructions that are stored in a memory. In an embodiment, a surgeon may input via the user interface 25 a selected power output, and the electrosurgical system 10 controls the probe 100 to automatically adjust the ablation volume by changing the operating frequency of the probe 100, e.g., based on the power level and/or level of reflected power.

Electrosurgical power generating source 28 may include an actuator 40. Actuator 40 may be any suitable actuator, e.g., a footswitch, a handswitch, an orally-activated switch (e.g., a bite-activated switch and/or a breath-actuated switch), and the like. Actuator 40 may be operably coupled to the processor by a cable connection (e.g., 17 shown in FIG. 1) or a wireless connection, e.g., a radiofrequency or infrared link. Electrosurgical power generating source 28 may include a database configured to store and retrieve energy applicator data, e.g., parameters associated with one or energy applicators. In use, the clinician may interact with the user interface 25 to preview operational characteristics of an energy-delivery device, such as, for example, probe 100.

User interface 25 may include a display device 21, e.g., a flat-panel graphic LCD (liquid crystal display), adapted to visually display one or more user-interface elements (e.g., 23 and 24 shown in FIG. 1). Display device 21 may include touchscreen capability, e.g., the ability to receive user input through direct physical interaction with the display device 21, e.g., by contacting the display panel of the display device 21 with a stylus or fingertip. A user-interface element (e.g., 23 and/or 24 shown in FIG. 1) may have a corresponding active region, such that, by touching the display panel within the active region associated with the user-interface element, an input associated with the user-interface element is received by the user interface 25. User interface 25 may include one or more controls 22, including without limitation a switch (e.g., pushbutton switch, toggle switch, slide switch) and/or a continuous actuator (e.g., rotary or linear potentiometer, rotary or linear encoder.) In an embodiment, a control 22 has a dedicated function, e.g., display contrast, power on/off, and the like. Control 22 may also have a function that may vary in accordance with an operational mode of the electrosurgical system 10. A user-interface element 23 may be positioned substantially adjacent to a control 22 to indicate the function thereof. Control 22 may also include an indicator, such as an illuminated indicator (e.g., a single- or variably-colored LED indicator).

Electrosurgical system 10 includes an inflow/outflow junction 51 coupled in fluid communication with the coolant supply system 150 via one or more coolant paths (e.g., 19 and 20 shown in FIG. 1), and coupled in fluid communication with the probe 100 via the flexible, fluid-cooled shaft 110. Coolant supply system 150 may be adapted to circulate coolant fluid "F" into and out of the inflow/outflow junction 51. Coolant source 18 may be any suitable housing containing a reservoir of coolant fluid "F", and may maintain coolant fluid "F" at a predetermined temperature. For example, the coolant source 18 may include a cooling unit (not shown) capable of cooling the returning coolant fluid "F" from the antenna assembly 12 via the shaft 110.

Coolant fluid "F" may be any suitable fluid that can be used for cooling the cable assembly 15 and/or cooling or buffering the probe 100, e.g., deionized water, or other suitable cooling medium. Coolant fluid "F" may have dielectric properties and may provide dielectric impedance buffering for the antenna assembly 12. Coolant fluid "F" composition may vary depending upon desired cooling rates and the desired tissue impedance matching properties. Various fluids may be used, e.g., liquids including, but not limited to, water, saline, perfluorocarbon, such as the commercially available Fluorinert® perfluorocarbon liquid offered by Minnesota Mining and Manufacturing Company (3M), liquid chlorodifluoromethane, etc. In other variations, gases (such as nitrous oxide, nitrogen, carbon dioxide, etc.) may also be utilized as the cooling fluid. In yet another variation, a combination of liquids and/or gases, including, for example, those mentioned above, may be utilized as the coolant fluid "F".

Coolant supply system 150 generally includes a first coolant path 19 leading from the coolant source 18 to the inflow/outflow junction 51, and a second coolant path 20 leading from the inflow/outflow junction 51 to the coolant source 18. In some embodiments, the first coolant path 19 includes a fluid-movement device 34 configured to move coolant fluid "F" through the first coolant path 19. The position of the fluid-movement device 34, e.g., in relation to the coolant source 18, may be varied from the configuration depicted in FIG. 1. Second coolant path 20 may additionally, or alternatively, include a fluid-movement device (not shown) configured to move coolant fluid "F" through the second coolant path 20. Examples of coolant supply system embodiments are disclosed in commonly assigned U.S. patent application Ser. No. 12/566,299 filed on Sep. 24, 2009, entitled "OPTICAL DETECTION OF INTERRUPTED FLUID FLOW TO ABLATION PROBE".

Figure 2A:
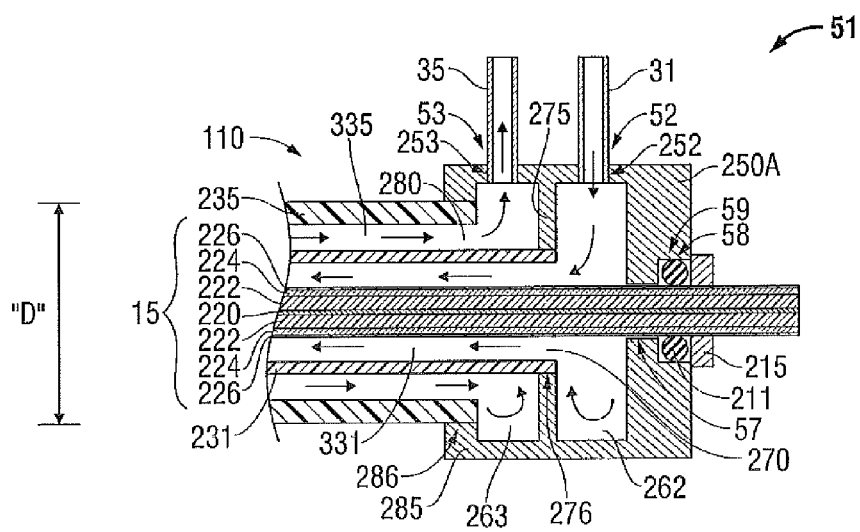
FIG. 2A is an enlarged, cross-sectional view of the indicated area of detail of FIG. 1 showing a portion of a flexible, fluid-cooled shaft and an inflow/outflow junction adapted to be coupled in fluid communication therewith in accordance with an embodiment of the present disclosure.

FIG. 2A shows an embodiment of the inflow/outflow junction 51 of the electrosurgical system 10 shown in FIG. 1. Inflow/outflow junction 51 is adapted to be fluidly coupleable with the inner tubular member 231 and the outer tubular member 235 of the flexible, fluid-cooled shaft 110, and adapted to be connected in fluid communication with the coolant supply system 150. Inflow/outflow junction 51 may have a variety of suitable shapes, e.g., cylindrical, rectangular or the like.

Inflow/outflow junction 51 generally includes a housing 250A having an outer wall 285 and an inner wall 275 defining a plurality of interior chambers and/or openings or ports therein. In some embodiments, the outer wall 285 and the inner wall 275 cooperatively define a fluid inlet chamber 262 and a fluid outlet chamber 263, which are described later in this disclosure.

Housing 250A generally includes a fluid inlet port 52, a fluid outlet port 53, and a cable-entry port 59 all defined therein. Cable-entry port 59 includes an opening or passage 57 defined in the outer wall 285 configured to receive the cable assembly 15 therethrough. Cable-entry port 59 may include a channel or groove 58 adapted to receive an o-ring 211 configured to provide a fluid seal between the housing 250A and the cable assembly 15. In some embodiments, a cable-movement restrictor 215 may be affixed to or integrally formed with the housing 250A. Cable-movement restrictor 215 may be adapted to restrict movement of the cable assembly 15 and/or adapted to fixedly or releaseably secure the cable assembly 15 to the housing 250A. Cable-movement restrictor 215 may include any suitable fastening element, e.g., clips, clamps, or adhesive.

Fluid inlet port 52 may be adapted to be connected in fluid communication with the first coolant path 19. Fluid outlet port 53 may be adapted to be connected in fluid communication with the second coolant path 20. In some embodiments, the first coolant path 19 includes a coolant supply line 31 leading from the coolant source 18 to the fluid inlet port 52, and the second coolant path 20 includes a coolant return line 35 leading from the fluid outlet port 53 to the coolant source 18. Fluid inlet port 52 and the fluid outlet port 53 may be disposed at any suitable location along the outer wall of the housing 205. Fluid inlet port 52 and the fluid outlet port 53 may have any suitable configuration, including without limitation nipple-type inlet fittings, compression fittings, and recesses, and may include an o-ring type elastomeric seal.

In an embodiment, the fluid inlet port 52 is configured to define a first recess 252 in the outer wall 285 of the housing 250A, and the fluid outlet port 53 is configured to define a second recess 253 in the outer wall 285. First recess 252 and the second recess 253 may be of any suitable shape, e.g., rectangular, cylindrical, etc., and may include a groove adapted to receive an O-ring or other suitable sealing element. In some embodiments, the coolant supply line 31 is sealably connected with and extends into the first recess 252, and the coolant return line 35 is sealably connected with and extends into the second recess 253.

Housing 250A may be adapted to allow a portion of the presently disclosed flexible, fluid-cooled shaft 110 (e.g., a portion of the inner tubular member 231 and the cable assembly 15) to extend through the fluid outlet chamber 263 and/or the fluid inlet chamber 262. Fluid outlet chamber 263 is disposed in fluid communication with the fluid outlet port 53, and may be configured to be coupleable with the outer tubular member 235 of the shaft 110. Fluid outlet chamber 263 generally fluidly connects the fluid outlet port 53 to the fluid outflow conduit 335. In an embodiment, the outer wall 285 of the housing 250A is configured to define an opening 280 in the fluid outlet chamber 263 to allow the fluid outlet chamber 263 to be connectable in fluid communication with the fluid outflow conduit 335.

Fluid inlet chamber 262 is disposed in fluid communication with the fluid inlet port 52, and may be configured to be coupleable with the inner tubular member 231 of the shaft 110. Fluid inlet chamber 262 generally fluidly connects the fluid inlet port 52 to the fluid inflow conduit 331. In an embodiment, the inner wall 275 of the housing 250A is configured to define an opening 270 in the fluid inlet chamber 262 to allow the inlet chamber 262 to be connectable in fluid communication with the fluid inflow conduit 331. The shape and size of the fluid outlet chamber 263 and the fluid inlet chamber 262 may be varied from the configuration depicted in FIG. 2A.

Housing 250A may be configured to be sealingly engageable with the inner tubular member 231, e.g., to fluidly connect the fluid inlet chamber 262 and the fluid inflow conduit 331, and/or sealingly engageable with outer tubular member 235, e.g., to fluidly connect the fluid outlet chamber 263 and the fluid outflow conduit 335. Opening 270 defined in the inner wall 275 may be configured to receive the inner tubular member 231. Inner wall 275 may include an engagement portion 276 configured to engage an outer surface of the inner tubular member 231. Sealing engagement between the engagement portion 276 and the outer surface of the inner tubular member 231 may be provided, for example, by a sealing element, e.g., an o-ring, associated with the engagement portion 276. Sealing engagement may be provided by way of threads, external or internal, disposed on or within the inner tubular member 231 and threads disposed within or on the engagement portion 276. It is to be understood, however, that sealing engagement between the engagement portion 276 and the outer surface of the inner tubular member 231 may be provided by any suitable sealing means.

Opening 280 defined in the outer wall 285 may be configured to receive the outer tubular member 235. Outer wall 285 may include an engagement portion 286 configured to engage an outer surface of the outer tubular member 235. Sealing engagement between the engagement portion 286 and the outer surface of the outer tubular member 235 may be provided, for example, by a sealing element, e.g., an o-ring, associated with the engagement portion 286 of the outer wall 285. Sealing engagement may be provided by way of threads, external or internal, disposed on or within the outer tubular member 235 and threads disposed within or on the engagement portion 286. It is to be understood, however, that sealing engagement between the engagement portion 286 and the outer surface of the outer tubular member 235 may be provided by any suitable sealing means.

Figure 2B:
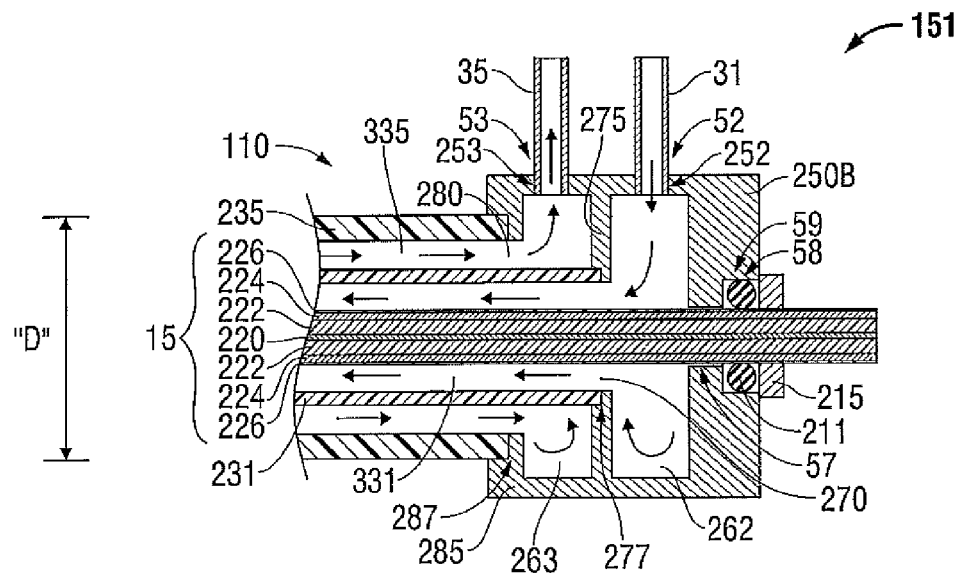
FIG. 2B is an enlarged, cross-sectional view of another embodiment of an inflow/outflow junction adapted to be coupled in fluid communication the flexible, fluid-cooled shaft of FIG. 1 in accordance with the present disclosure.

FIG. 2B shows an inflow/outflow junction 151 in accordance with the present disclosure. Inflow/outflow junction 151 includes a housing 250B that is similar to the housing 250A shown in FIG. 2A except for the configuration of the engagement portion 277 of the inner wall 275 and the configuration of the engagement portion 287 of the outer wall 285.

Engagement portion 277 is adapted to engage the outer surface of the inner tubular member 231 (e.g., similar to the engagement portion 276 shown in FIG. 2A). Engagement portion 277 includes a protrusion extending outwardly from the inner wall 275 adapted to engage an end portion of the inner tubular member 231. Inner tubular member 231 and the engagement portion 277 may be sealingly connected in any suitable fashion, e.g., by a heat-resistant adhesive material, or other suitable sealing material.

Engagement portion 287 is adapted to engage the outer surface of the outer tubular member 235 (e.g., similar to the engagement portion 286 shown in FIG. 2A). Engagement portion 287 includes a protrusion extending outwardly from the outer wall 285 adapted to engage an end portion of the outer tubular member 235. Outer tubular member 235 and the engagement portion 287 may be sealingly connected with a heat-resistant adhesive material, or other suitable sealing material.

Figure 2C:
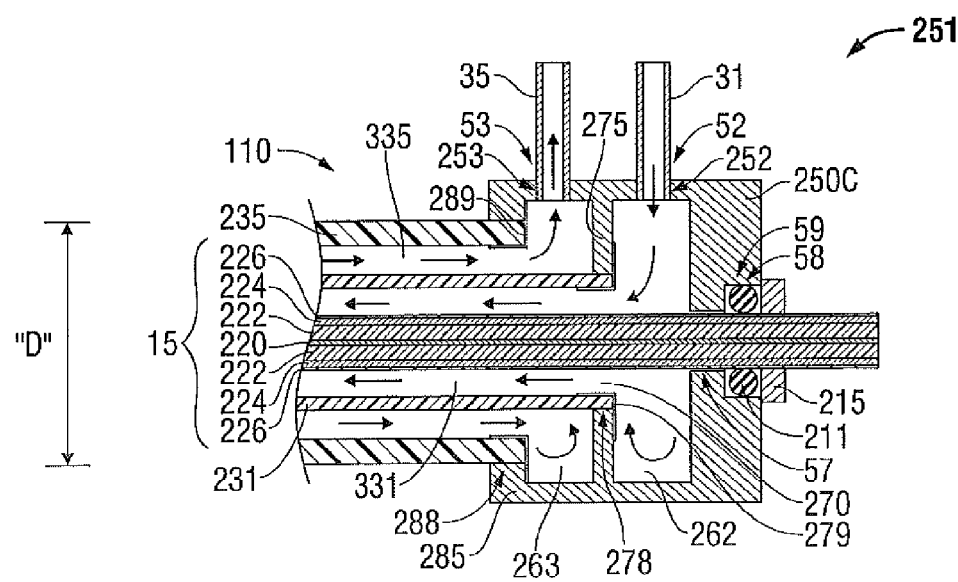
FIG. 2C is an enlarged, cross-sectional view of yet another embodiment of an inflow/outflow junction adapted to be coupled in fluid communication the flexible, fluid-cooled shaft of FIG. 1 in accordance with the present disclosure.

FIG. 2C shows an inflow/outflow junction 251 in accordance with the present disclosure. Inflow/outflow junction 251 includes a housing 250C that is similar to the housing 250A shown in FIG. 2A except for the configuration of the engagement portion 278 of the inner wall 275 and the configuration of the engagement portion 288 of the outer wall 285.

Engagement portion 278 is adapted to engage the outer surface of the inner tubular member 231 (e.g., similar to the engagement portion 276 shown in FIG. 2A). Engagement portion 278 includes a generally L-shaped bracket 279 coupled to the inner wall 275 adapted to engage an end portion and the inner surface of the inner tubular member 231.

Engagement portion 288 is adapted to engage the outer surface of the outer tubular member 235 (e.g., similar to the engagement portion 286 shown in FIG. 2A). Engagement portion 288 includes a generally L-shaped bracket 289 coupled to the outer wall 285 adapted to engage an end portion and the inner surface of the outer tubular member 235.

FIG. 3 shows an embodiment of the probe 100 of the electrosurgical system 10 shown in FIG. 1. Probe 100 generally includes an antenna assembly 12 having a distal radiating portion "R" disposed within a chamber 338 (also referred to herein as a coolant chamber) defined by an end-cap assembly 360. Antenna assembly 12, which is described in more detail later in this disclosure, includes a proximal arm 370 and a distal arm 380.

End-cap assembly 360 includes a connector portion 368 and an end cap 364 disposed at the distal end of the connector portion 368 and coupled thereto. End cap 364 generally defines an interior chamber 365 therein. Connector portion 368 includes a substantially tubular, body member 361 defining an interior lumen disposed in fluid communication with the interior chamber 365 of the end cap 364. Connector portion 368 includes a distal portion 363, e.g., adapted for connection to the end cap 364, and a proximal portion 362, e.g., adapted for connection to the outer tubular member 235 of the shaft 110. The shape and size of the distal portion 363 and the proximal portion 362 of the connector portion 368 may be varied from the configuration depicted in FIG. 3.

Connector portion 368 may be formed of any suitable material. In some embodiments, the connector portion 368 may be formed of a composite material having low electrical conductivity, e.g., glass-reinforced polymers or ceramics. Outer tubular member 235 and the proximal portion 362 of the connector portion 368 may be sealingly connected with a heat-resistant adhesive material 302, or other suitable sealing material.

End cap 364 includes a tapered portion 320, which may terminate in a sharp tip 323 to allow for insertion into tissue with minimal resistance. Tapered portion 320 may include other shapes, such as, for example, a tip 323 that is rounded, flat, square, hexagonal, or cylindroconical. End cap 364 may be formed of a material having a high dielectric constant, and may be a trocar, e.g., a zirconia ceramic. In some embodiments, an interior chamber 365 defined by the end cap 364 includes a proximal chamber portion 366 and a distal chamber portion 367 fluidly coupled to the proximal chamber portion 366. The shape and size of the proximal chamber portion 366 and the distal chamber portion 367 may be varied from the configuration depicted in FIG. 3.

Probe 100 may be provided with a removable, protective cap 390 configured to cover at least a portion of the end-cap assembly 360. In some embodiments, the protective cap 390 is configured to cover the end cap 364. Protective cap 390 may be removeably disposed over the end cap 364 during deployment of the probe 100, e.g., to avoid injuring tissue. Protective cap 390 may be formed of any suitable material, e.g., plastic, by any suitable process.

Connector portion 368 may be adapted for releasable connection to the protective cap 390. In some embodiments, the distal end of the connector portion 368 and the proximal end of the protective cap 390 are releasably connectable by a screw-fitted connection. In an embodiment, the distal end of the connector portion 368 is provided with a series of external threads 369 configured to matingly engage with a series of internal treads 393 disposed at the proximal end of the protective cap 390. It will be appreciated that the proximal end of the protective cap 390 may be provided with external threads and the connector portion 368 may be provided with internal treads. It is to be understood that the protective cap 390 may be releasably connectable to the connector portion 368 in any suitable fashion.

Antenna assembly 12 includes a proximal arm 370 and a distal arm 380. Proximal arm 370 may have any suitable length "L2", and the distal arm 380 may have any suitable length "L3". In some embodiments, the proximal arm 370 may have a length "L2" in a range from about 0.05 inches to about 0.50 inches. In some embodiments, the distal arm 380 may have a length "L3" in a range from about 0.05 inches to about 0.50 inches.

Proximal arm 370 and the distal arm 380 may be formed of any suitable electrically-conductive material, e.g., metal such as stainless steel, aluminum, titanium, copper, or the like. In some embodiments, the proximal arm 370 is constructed from a piece of stainless steel, and may be coated in a high electrical conductivity, corrosion-resistant metal, e.g., silver, or the like. The proximal end 371 of the proximal arm 370 is electrically coupled to the distal end 325 of the outer conductor 224, e.g., by solder or other suitable electrical connection. In some embodiments, the proximal end 371 of the proximal arm 370 is coaxially disposed about the distal end 325 of the outer conductor 224. Proximal arm 370 generally defines a first chamber or cavity 372 therein longitudinally extending from the distal end 325 of the outer conductor 224. A dielectric material 310 may be disposed within the first cavity 372.

Distal arm 380 includes a proximal portion 381 and a distal portion 383. The distal portion 383 of the distal arm 380 is at least partially disposed within a cavity defined by the end cap 364. Distal arm 380 has a stepped configuration, such that the outer diameter of the distal portion 383 is less than the outer diameter of the proximal portion 381. In some embodiments, the proximal chamber portion 366 of the interior chamber 365 defined by the end cap 364 may be configured to receive the proximal portion 381 of the distal arm 380 therein, and the distal chamber portion 367 of the interior chamber 365 defined by the end cap 364 may be configured to receive the distal portion 383 of the distal arm 380 therein. Proximal chamber portion 366 and/or the distal chamber portion 367 may be adapted to allow coolant fluid (e.g., "F" shown in FIG. 1) to circulate around the proximal portion 381 and/or the distal portion 383.

In some embodiments, the distal arm 380 is constructed from a machined piece of stainless steel, and may be coated in a high electrical conductivity, corrosion-resistant metal, e.g., silver, or the like. The proximal portion 381 of the distal arm 380 defines a second chamber or cavity 382 therein. Dielectric material 310 may be disposed within the second cavity 382. The distal portion 383 of the distal arm 380 defines a third chamber or cavity 384 therein. Inner conductor 220 extends at least partially therethrough. Inner conductor 220 may be electrically coupled to the distal portion 383 by solder 307. In some embodiments, the distal portion 383 of the distal arm 380 includes one or more solder holes 389 defined therethrough.

Distal arm 380 and the proximal arm 370 align at a junction member 311 (which is generally made of a dielectric material 310) and are also supported by the inner conductor 220 that extends at least partially through the distal radiating portion "R". Junction member 311 may be formed of low-loss plastic or any suitable elastomeric or ceramic dielectric material by any suitable process. In some embodiments, the junction member 311 is formed by overmolding and includes a thermoplastic elastomer, such as, for example, polyether block amide (e.g., Pebax®, manufactured by The Arkema Group of Colombes, France), polyetherimide (e.g., Ultem® and/or Extern®, manufactured by SABIC Innovative Plastics of Saudi Arabia) and/or polyimide-based polymer (e.g., Vespel®, manufactured by E. I. du Pont de Nemours and Company of Wilmington, Del., United States). Distal arm 380 and the proximal arm 370 may be insert molded with the junction member 311, such that the distal arm 380 and the proximal arm 370 are rigidly joined and spaced apart by the junction member 311, defining a feed gap "G" therebetween. In some embodiments, the feed gap "G" may be from about 1 mm to about 3 mm.

Probe 100 may include a balun structure "B" having a suitable length "L1". Balun structure "B" is disposed proximal to and spaced apart a suitable length from the antenna assembly 12. In some embodiments, the balun structure "B" may be a quarter-wavelength, ¼ λ, sleeve balun, or a ¾ λ sleeve balun. Odd harmonics (e.g., ¼ λ, ¾ λ, etc.) may cause a current null at the balun entrance, which may maintain a desired radiation pattern.

Balun structure "B" includes a balun insulator 340 disposed about the outer conductor 224 of the cable assembly 15, and an electrically-conductive layer 350 (also referred to herein as a conductive balun sleeve) disposed about the balun insulator 340, or portions thereof. A portion 345 of the balun insulator 340 may extend distally beyond the distal end 355 of the electrically-conductive member 350, e.g., to enhance microwave performance of the probe 100 and/or provide a desired ablation pattern. Conductive balun sleeve 350 may be formed as a single structure and electrically coupled to the outer conductor 224, e.g., by solder or other suitable electrical connection. In some embodiments, the proximal end 352 of the conductive balun sleeve 350 may be adapted to allow for connection, e.g., electrically and mechanically, to the outer conductor 224.

Balun structure "B", according to the embodiment shown in FIG. 3, includes a balun short 351 disposed at the proximal end of the balun insulator 340. Balun short 351 may be formed of any suitable electrically-conductive materials, e.g., copper, gold, silver or other conductive metals or metal alloys. In some embodiments, the balun short 351 has a generally ring-like or truncated tubular shape. Balun short 351 is electrically coupled to the outer conductor 224 of the feedline or cable assembly 15 by any suitable manner of electrical connection, e.g., soldering, welding, or laser welding. Balun short 351 is electrically coupled to the balun outer conductor 350 by any suitable manner of electrical connection.

Balun insulator 340 may be formed of any suitable insulative material, including, but not limited to, ceramics, water, mica, polyethylene, polyethylene terephthalate, polyimide, polytetrafluoroethylene (PTFE) (e.g., Teflon®, manufactured by E. I. du Pont de Nemours and Company of Wilmington, Del., United States), glass, metal oxides or other suitable insulator, and may be formed in any suitable manner. Balun insulator 340 may be grown, deposited or formed by any other suitable technique. In some embodiments, the balun insulator 340 is formed from a material with a dielectric constant in the range of about 1.7 to about 10.

Electrically-conductive layer 350 may be formed of any suitable electrically-conductive material, e.g., metal such as stainless steel, titanium, copper, etc., and may be formed in any suitable manner. In some embodiments, the electrically-conductive layer 350 has a length of about 0.1 inches to about 3.0 inches. The shape and size of the conductive balun sleeve 350 and balun insulator 340 may be varied from the configuration depicted in FIG. 3.

Probe 100 generally includes a coolant chamber 338 defined about the antenna assembly 12. Coolant chamber 338 is adapted to circulate coolant fluid (e.g., "F" shown in FIG. 1) around the antenna assembly 12 (as generally indicated by the arrows in FIG. 3) and disposed in fluid communication with the fluid inflow conduit 331 and the fluid outflow conduit 335. In some embodiments, the coolant chamber 338 is defined by the end-cap assembly 360 and includes an interior lumen defined by the substantially tubular, body member 361 of the connector portion 368. Coolant chamber 338 may additionally, or alternatively, include an interior chamber 365 defined by the end cap 364. The shape and size of the coolant chamber 338 may be varied from the configuration depicted in FIG. 3.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or surgically, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Treatment of certain tumors may involve probe repositioning during the ablation procedure, such as where the tumor is larger than the probe or has a shape that does not correspond with available probe geometry or radiation pattern.

In operation, microwave energy having a wavelength, lambda (λ), is transmitted through the antenna assembly 12, e.g., along the proximal arm 370 and the distal arm 380, and radiated into the surrounding medium, e.g., tissue. The length of the antenna for efficient radiation may be dependent on the effective wavelength, λeff, which is dependent upon the dielectric properties of the treated medium. Antenna assembly 12 through which microwave energy is transmitted at a wavelength, λ, may have differing effective wavelengths, λeff, depending upon the surrounding medium, e.g., liver tissue, as opposed to breast tissue.

Figure 4:
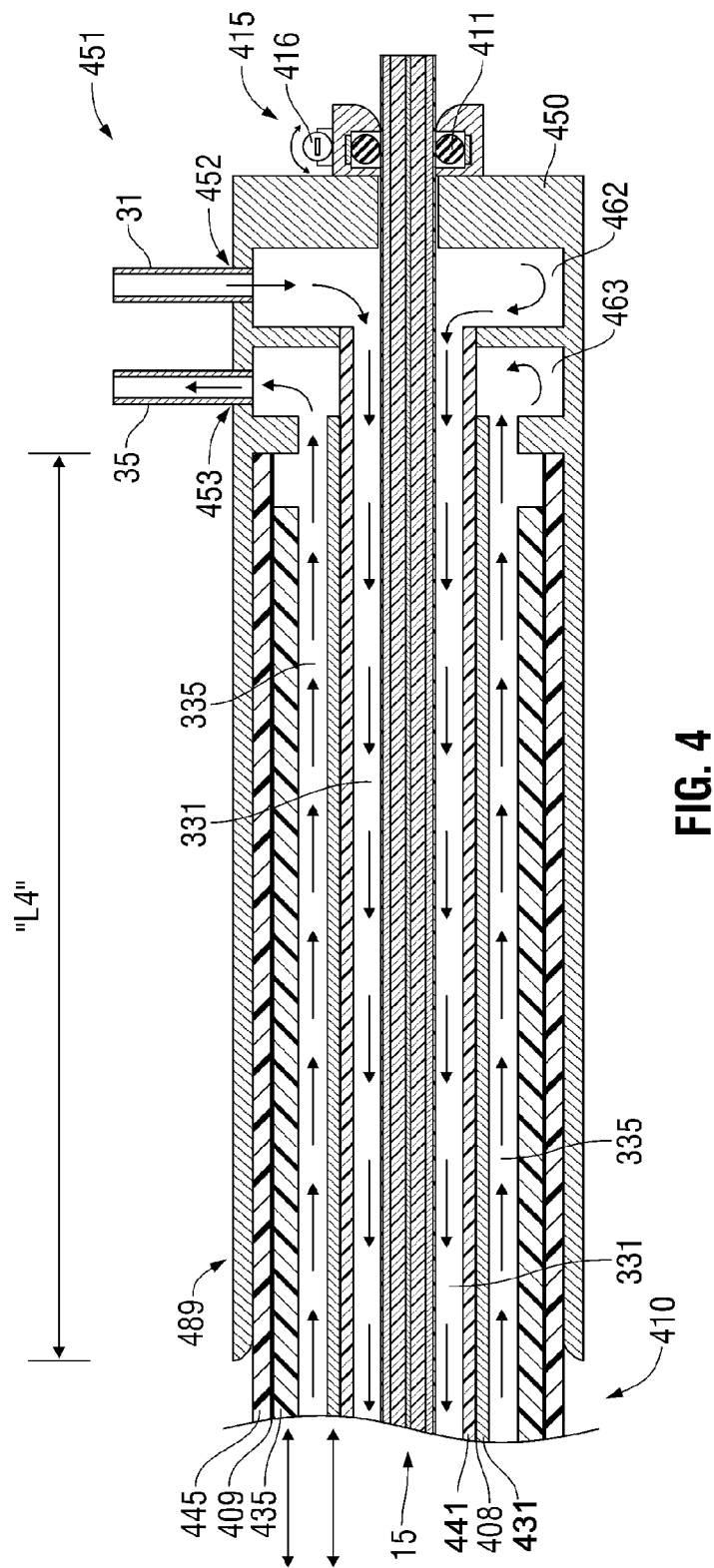
FIG. 4 is a cross-sectional view of a portion of a flexible, extendable/retractable fluid-cooled shaft and an inflow/outflow junction adapted to be coupled in fluid communication therewith in accordance with an embodiment of the present disclosure.

FIG. 4 shows an inflow/outflow junction 451 adapted to be connected in fluid communication with a portion of a flexible, extendable/retractable fluid-cooled shaft 410 according to an embodiment of the present disclosure. Inflow/outflow junction 451 includes a housing 450 configured to be releaseably and sealably coupleable with the cable assembly 15 shown in FIG. 1. Housing 450 includes a fluid inlet port 452, a fluid outlet port 453, a fluid inlet chamber 462, a fluid outlet chamber 463, a tubular sleeve member 489, and a releasable, cable-movement restrictor 415.

Releasable, cable-movement restrictor 415 includes a sealing element 411, e.g., an o-ring, and a rotatable member 416. In some embodiments, rotation of the rotatable member 416 in a first direction (e.g., a clockwise direction) effects a compression force on the sealing element 415 to restrict movement of the cable assembly 15 and to provide a fluid seal. In some embodiments, rotation of the rotatable member 416 in a second direction (e.g., a counter-clockwise direction) releases the compression force on the sealing element 411 to allow movement of the cable assembly 15, thereby allowing extension and/or retraction of the outer tubular member 445 and the inner tubular member 441 of the shaft 410.

Tubular sleeve member 489 of the presently disclosed housing 450 is generally configured to house a portion of the expandable/retractable shaft 410, and may have any suitable length "L4". Fluid inlet port 452, fluid outlet port 453, fluid inlet chamber 462, and fluid outlet chamber 463 shown in FIG. 4 are similar to the fluid inlet port 52, fluid outlet port 53, fluid inlet chamber 262, and fluid outlet chamber 263 shown in FIG. 1, respectively, and further description thereof is omitted in the interests of brevity.

Flexible, extendable/retractable fluid-cooled shaft 410 is adapted to allow for selective adjustment of the length of the fluid-cooled shaft 410. In some embodiments, the shaft 410 may be selectively adjustable to any length between a first length (e.g., "L5" shown in FIG. 5), when the shaft 410 is in its most retracted use configuration, and a second length (e.g., "L6" shown in FIG. 5) when the shaft 410 is in its most extended use configuration. Flexible, extendable/retractable fluid-cooled shaft 410 generally includes an inlet sleeve 431, an outlet sleeve 435, an inner tubular member 441 coaxially disposed about and slideably coupled to the inlet sleeve 431, and an outer tubular member 445 coaxially disposed about and slideably coupled to the outlet sleeve 435. In some embodiments, a first lubricous sleeve 408 may be disposed between the inner tubular member 441 and the inlet sleeve 431, and a second lubricous sleeve 409 may be disposed between the outer tubular member 445 and the outlet sleeve 435.

First lubricous sleeve 408 and the second lubricous sleeve 409 may be formed of any suitable non-conductive insulator, e.g., a TEFLON® sleeve. First lubricous sleeve 408 and/or the second lubricous sleeve 409 may be selected based on materials properties, e.g., density and lubricity, to allow for sliding of the inner tubular member 441 over the inlet sleeve 431 and/or sliding of the outer tubular member 445 over outlet sleeve 435. First lubricous sleeve 408 and/or the second lubricous sleeve 409 may additionally, or alternatively, be selected to prevent damage and/or minimize wear to the inner tubular member 441 and/or the outer tubular member 445. First lubricous sleeve 408 and/or the second lubricous sleeve 409 may be formed of a lubricous polymeric material, such as a high-density polyolefin (e.g., polyethylene), polytetrafluoroethylene (a.k.a. PTFE or TEFLON®, manufactured by E. I. du Pont de Nemours and Company of Wilmington, Del., United States), or polyurethane. First lubricous sleeve 408 and/or the second lubricous sleeve 409 may be formed by heat-shrinkage, extrusion, molding, dip coating, or other suitable process. In some embodiments, the insulator sleeve 270 may include a surface coating formed of highly hydrophilic, low-friction polymer, such as polyvinylpyrrolidone, polyethyleneoxide, polyhydroxyethylmethacrylate, or copolymers thereof.

In some embodiments, the shaft 410 may be configured in its most retracted use configuration when the proximal end of the inner tubular member 441 is disposed proximally in substantial alignment with the proximal end of the inlet sleeve 431 and/or the proximal end of the outer tubular member 445 is disposed proximally in substantial alignment with the proximal end of the outlet sleeve 435.

FIG. 5 shows the flexible, extendable/retractable fluid-cooled shaft 410 and the inflow/outflow junction 451 of FIG. 4 in its most retracted use configuration in accordance with an embodiment of the present disclosure. In its most retracted use configuration, the fluid-cooled shaft 410 may have any suitable length "L5". In some embodiments, the flexible, extendable/retractable fluid-cooled shaft 410 may be provided with one or more shape-retention elements 510 adapted to provide resistance to change in the outer diameter of the shaft 410, e.g., during expansion/retraction of the shaft 410 and/or during the circulation of coolant fluid therethrough. Shape-retention elements 510 may be disposed around the outer tubular member 445 and/or slideably coupled to the outer tubular member 445.

FIG. 6 shows the flexible, extendable/retractable fluid-cooled shaft 410 and the inflow/outflow junction 451 of FIG. 4 in its most extended use configuration in accordance with an embodiment of the present disclosure. In its most retracted use configuration, the fluid-cooled shaft 410 may have any suitable length "L6".

The presently disclosed energy-delivery devices with a flexible, fluid-cooled shaft are capable of directing energy into tissue, and may be suitable for use in a variety of procedures and operations. The above-described energy-delivery device embodiments may be suitable for utilization with hand-assisted, endoscopic and laparoscopic surgical procedures. The above-described energy-delivery device embodiments may be suitable for utilization in open surgical applications.

Various embodiments of the presently disclosed energy-delivery device with a flexible, fluid-cooled shaft may allow the surgeon to deploy an ablation probe, e.g., between closely spaced boundaries of tissue structures, to reach the location of the ablation site. The above-described energy-delivery device embodiments may allow the surgeon to manually deploy an ablation probe having a flexible, fluid-cooled shaft with his/her hand to place the probe at difficult-to-reach locations, such as, for example, the dome of the liver near the top of the diaphragm. Various embodiments of the presently disclosed energy-delivery devices with a flexible, fluid-cooled shaft including a length of cable assembly surrounded by inner and outer tubular members adapted to circulate coolant fluid therethrough may lessen the potentially unwanted heat transfer from the cable assembly to the patient's body during a procedure, e.g., an ablation procedure.

The above-described inflow/outflow junction embodiments are adapted to be coupled in fluid communication with the inner and outer tubular members of the above-described flexible, fluid-cooled shaft embodiments, and adapted to be coupled in fluid communication with a suitable coolant supply system. The presently disclosed inflow/outflow junctions embodiments may be adapted to be coupled in fluid communication with a coolant supply system and adapted to selectively allow movement of a cable assembly therethrough, e.g., to facilitate the extension/retraction of an extendable/retractable fluid-cooled shaft.

Electrosurgical systems including an energy-delivery device with a flexible, fluid-cooled shaft according to embodiments of the present disclosure may be fluidly coupled to a coolant supply system via the above-described inflow/outflow junction embodiments.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A treatment device comprising:
   a housing defining an aperture on a proximal end thereof, an inlet chamber, and an outlet chamber, the housing including a tubular sleeve member extending from a distal portion thereof;
   a cable assembly disposed within the housing via the aperture, the cable assembly including an inner conductor, an outer conductor, and a dielectric material disposed between the inner conductor and the outer conductor; and
   a fluid-cooled shaft slidingly coupled to the tubular sleeve member of the housing and in fluid communication with the inlet chamber and the outlet chamber of the housing, the fluid-cooled shaft including an inlet sleeve slidingly coupled to an inner tubular member.

2. The treatment device according to claim 1, further comprising an outer tubular member coupled to the housing and disposed within the tubular sleeve member, the outer tubular member defining an outflow conduit fluidly coupled to the outlet chamber.

3. The treatment device according to claim 1, wherein the inner tubular member is coupled to the housing and defines an inflow conduit fluidly coupled to the inlet chamber.

4. The treatment device according to claim 2, further comprising an outlet sleeve slidingly coupled to the outer tubular member and configured to selectively adjust a length of the fluid-cooled shaft.

5. The treatment device according to claim 1, wherein the cable assembly is configured to couple to an antenna assembly, the antenna assembly configured to transmit microwave energy.

6. The treatment device according to claim 4, further comprising a lubricious sleeve disposed between the outer tubular member and the outlet sleeve, the lubricous sleeve configured to facilitate sliding of the outlet sleeve relative to the inner tubular member.

7. The treatment device according to claim 1, further comprising a lubricious sleeve disposed between the inner tubular member and the inlet sleeve, the lubricous sleeve configured to facilitate sliding of the inlet sleeve relative to the outer tubular member.

8. The treatment device according to claim 2, further comprising at least one shape-retention element disposed around at least a portion of the outer tubular member.

9. The treatment device according to claim 8, wherein the at least one shape-retention element is disposed on a distal portion of the outer tubular member.

10. The treatment device according to claim 4, wherein movement of the outlet sleeve relative to the outer tubular member causes the length of an exposed portion of the fluid-cooled shaft to change.

11. The treatment device according to claim 1, wherein distal movement of the cable assembly relative to the housing causes distal movement of the fluid-cooled shaft relative to the housing.

12. The treatment device according to claim 1, further comprising a power generating source coupled to the cable assembly.

13. The treatment device according to claim 1, wherein the cable assembly includes a balun structure disposed on at least a portion of the cable assembly, the balun structure including a balun insulator and a conductive balun sleeve disposed around an outer surface of the balun insulator.

14. The treatment device according to claim 13, wherein the balun insulator is formed of at least one of ceramic, water, mica, polyethylene, polyethylene terephthalate, polyimide, polytetrafluoroethylene, glass, metal oxides, or any combination thereof.

15. A system comprising:
   a power generating source configured to generate electrosurgical energy; and
   a treatment device including:
      a housing defining an aperture on a proximal end thereof, an inlet chamber, and an outlet chamber, the housing including a tubular sleeve member extending from a distal portion thereof;
      a cable assembly disposed within the housing via the aperture, the cable assembly including an inner conductor, an outer conductor, and a dielectric material disposed between the inner conductor and the outer conductor; and
      a fluid-cooled shaft slidingly coupled to the tubular sleeve member of the housing and in fluid communication with the inlet chamber and the outlet chamber of the housing, the fluid-cooled shaft including an inlet sleeve slidingly coupled to an inner tubular member.

16. The system according to claim 15, wherein the treatment device further comprises an outer tubular member coupled to the housing and disposed within the tubular sleeve member, the outer tubular member defining an outflow conduit fluidly coupled to the outlet chamber.

17. The system according to claim 15, wherein the inner tubular member is coupled to the housing and defines an inflow conduit fluidly coupled to the inlet chamber.

18. The system according to claim 16, wherein the treatment device further comprises an outlet sleeve slidingly coupled to the outer tubular member and configured to selectively adjust a length of the fluid-cooled shaft.

19. The system according to claim 15, wherein the cable assembly is configured to connect an antenna assembly to the power generating source.

* * * * *